United States Patent [19]

Barker

[11] 4,116,049
[45] Sep. 26, 1978

[54] METHOD FOR MEASURING PLANE STRAIN FRACTURE TOUGHNESS

[75] Inventor: Lynn Marshall Barker, Salt Lake City, Utah

[73] Assignee: Terra Tek, Inc., Salt Lake City, Utah

[21] Appl. No.: 805,312

[22] Filed: Jun. 10, 1977

[51] Int. Cl.² ............................................. G01N 3/08
[52] U.S. Cl. ...................................................... 73/87
[58] Field of Search ...................... 73/87, 95, 88 R, 96

[56] References Cited

U.S. PATENT DOCUMENTS 3,538,757  11/1970  Osborne ............................... 73/96 X

*Primary Examiner*—Jerry W. Myracle
*Attorney, Agent, or Firm*—M. Reid Russell

[57] ABSTRACT

The present invention consists of a method for accurately measuring the plane strain fracture toughness of ductile and brittle materials, the method to be practiced on a specimen formed such that, when the specimen is appropriately loaded, a crack will initiate at a predetermined point or line, with such crack formed thereat being intrinsically stable such that the load executed on the specimen must be continually increased in order to further advance the crack along a predetermined path through the specimen, until, at some critical location along the predetermined crack path, the load necessary to further advance the crack reaches a maximum, thereafter decrasing as the crack advances beyond the critical location along the remainder of its predetermined path through the specimen, that critical location being essentially independent of the specimen material, it being determined by the specimen geometry alone as long as elastic plane strain conditions prevail in the specimen sufficiently close to the crack tip.

The method of the present invention involves taking the specimen through an appropriate loading sequence and determining the critical (or maximum) load that occurs when the crack passes through the critical position. With that data, the plane strain critical stress intensity factor, $K_{IC}$, or fracture toughness for the specimen material, can be calculated mathematically considering the critical load, the specimen size and geometry, taking into account the Poisson's ratio of the specimen material, but without necessitating reference to any other standard specimen or fracture toughness test results thereon.

4 Claims, 7 Drawing Figures

METHOD FOR MEASURING PLANE STRAIN FRACTURE TOUGHNESS

BACKGROUND OF THE INVENTION

1. Field of the Invention

This invention relates to new and useful improvements in methods for measuring the fracture toughness of a ductile or brittle specimen material.

2. Prior Art

Plane strain fracture toughness measurement techniques making use of the principles of linear elastic fracture mechanics have been developed over about the last two decades. Such methods have generally involved introduction of a crack into an appropriate specimen configuration, a measurement of the crack position, a measurement of the load necessary to cause the crack to advance, and a measurement or a calculation of the rate of change of the specimen's compliance with respect to the distance of crack propagation.

Drawbacks to present fracture toughness measurement techniques that are overcome by the present invention include: that it is usually very difficult to introduce a real crack into a specimen of brittle material; such experiments and data collection therefrom have, heretofore, been complicated; and such experiments have required that both the crack position and the crack-advancing load must be measured during the experiment.

Reference is hereby made to a patent entitled "Fracture Toughness Test Method," by the present inventor, Lynn M. Barker, which patent is assigned to and filed by Reed Tool Company, Houston, Tex. This patent deals with an Improved Method for Testing Fracture Toughness of Tungsten Carbide Samples. Unlike the present invention, the method taught by this process involves comparing the results of identical tests run on two specimens of identical size and shape but of different materials, and hence only comparative results are obrtained from this procedure. The present invention, unlike the above cited application for patent, produces a measurement of the actual megapascal times square root meter, or psi times square root inch, value of the critical stress intensity factor (fracture toughness) of a specimen material. While the present invention, like the above cited application for patent, can be used for testing of tungsten carbide samples, it should be understood that the present invention is not limited to tungsten carbide samples only, and encompasses a determination of the fracture toughness of a specimen from consideration of: the peak or critical load executed on the sample, the sample geometry and size, and Poisson's ratio, for the specimen only. Further, the method of the present invention is suitable for testing of many other brittle and ductile materials. The present invention is therefore not limited, as is the above cited patent application, to brittle materials only and does not require data comparison with a standard specimen.

Testing procedures and practices involving testing of crack growth stability in ductile and brittle materials have been recorded in works like that of H. G. Tattersall and G. Tappin, "The Work of Fracture and its Measurement in Metals, Ceramics, and Other Materials." J. of Mater. Sci 1, 296 (1966). As reported therein, the procedures have involved a segment of a rod specimen, the specimen having a notch cut therein leaving a triangular cross-sectional remainder across a central crack plane such that a crack started at the apex of that triangular remainder will continue to widen uniformly as it is propagated through the specimen with incremental increases in the bending stresses applied to the sample. The results of such testing enabled the authors to calculate fracture toughness by integrating the load-deflection curve for the material. That work, however, did not involve a determination of the fracture toughness of a specimen from consideration of the peak or critical load exerted on the sample; the sample geometry; the sample size; and Poisson's ratio, for the specimen only.

A number of other investigations have been undertaken involving stable crack growth. Some such references include: S. Mostovoy, R. P. Crosley, and E. J. Ripling, "Use of Crack-Line Load Specimens for Measuring Plane-Strain Fracture Toughness," J. Mater. 2, 66 (1967); H. L. Marcus and G. C. Sih, "A Crackline-Loaded Edge-Crack Stress Corrosion Specimen," Eng. Frac. Mech. 3, 453 (1971); J. P. Gallagher, "Experimentally Determined Stress Intensity Factors for Several Contoured Double Cantilever Beam Specimens," Eng. Frac. Mech. 3, 27 (1971); J. A. Kies and A. B. J. Clark, in *Proceedings of the Second International Conference on Fracture,* paper 41, Brighton (1969); A. G. Evans, "A Method for EValuating the Time-Dependent Failure Characteristics of Brittle Materials — And its Application to Polycrystaline Alumina," J. Mater. Sci. 7, 1137 (1972); R. C. Clifton, E. R. Simonson, A. H. Jones and S. J. Green, "Determination ofthe Critical Stress Intensity Factor $K_{IC}$ from Internally-Pressurized Thick-Walled Vessels," published in Experimental Mechanics. None of these references or any reference known to the inventor, has, however, involved, as does the present invention, the measurement of fracture toughness from considerations of only the peak (critical) load, the specimen geometry, the specimen size, and Poisson's ratio, for the specimen material.

Within the knowledge of the inventor, the method and technique of the present invention is unlike any heretofore known, and is therefore, believed to be both novel and unique.

SUMMARY OF THE INVENTION

It is the principal object of the present invention to provide a simple method for measuring the plane strain fracture toughness of a ductile or brittle material.

Another object of the present invention is to provide a simple method for calculating the plane strain fracture toughness of a ductile or brittle specimen from the peak or critical load required to advance a crack in the specimen through the critical location therein considering only that critical load, the specimen geometry, specimen size, and the Poisson's ratio of the specimen material.

Still another object of the present invention is to provide a method for measuring the plane strain fracture toughness of a ductile or brittle specimen involving testing of the single specimen only.

Principal steps in practicing the present invention in a method for measuring the plane strain fracture toughness of ductile and brittle materials first involve the preparation of a specimen of a material to be tested. That specimen should be prepared so as to insure that: when the specimen is appropriately loaded, a crack will initiate at a predetermined point or line and will propagate along a predetermined path through the specimen; during an initial loading phase of an experiment conducted on the specimen, which loading may or may not include the initiation of a crack in that specimen, crack growth will be intrinsically stable, even in a specimen formed from a very brittle material, necessitating the loading on the specimen be continually increased in order to further advance the crack; at some crack location within the specimen there exists a critical point or location whereat, from that point, the crack will progress through the specimen with decreasing loading, which crack location is at a point along the predetermined crack path through the specimen; the specimen's critical point is essentially independent of the specimen material, that point being determined essentially by the specimen geometry, as long as the specimen is of or larger than a certain size, and the loading conditions on the specimen, at the tip of the crack, are primarily plane strain conditions.

To practice the method of the invention the specimen is attached to an appropriate machine for subjecting it to a load necessary to initiate and advance a crack along the predetermined path through the specimen. During the initial phase of the procedure the crack is started, and thereafter, with increased loading, uniform crack growth occurs with incremental increases in load, until the crack reaches the critical location along the predetermined crack path through the specimen. That critical location comprises a point of critical or greatest load, and thereafter, the load on the specimen will decrease as further crack growth occurs. The critical load is measured by some appropriate sensing arrangement and thereafter the plane strain critical stress intensity factor is calculated from the single testing procedure conducted on the single specimen by correlating that measured peak load with the specimen geometry, the specimen size and the Poisson's ratio for the specimen material.

Further objects and procedures in practicing the method of the present invention will become apparent from the following detailed description taken together with the accompanying drawings.

THE DRAWINGS

FIG. 1 is an example of a slotted short rod specimen that is preferred for use in practicing the method of the present invention;

FIG. 2, a machine for providing a plane strain loading to a specimen like the specimen of FIG. 1, which specimen is shown installed therewith;

FIG. 3, a side elevation schematic view of a jaw portion of the machine of FIG. 2 with the specimen shown installed thereto;

FIG. 4, a graph relating an applied load exerted on a specimen during practice of the method of the present invention in relation to time; and FIG. 5(a), a top plan sectional view of the sample shown in FIG. 3 taken along the line 5—5 therein, showing a crack as having progressed partly through that specimen, and a crack advance increment, da;

FIG. 5(b), a side elevation view of the specimen of FIG. 3, shown removed for the machine of FIG. 2; and FIG. 5(c), a graph showing load versus load-point-opening paths of the specimen.

DETAILED DESCRIPTION

Referring now to Drawings.

The present invention consists of a method and procedure for measuring the plane strain fracture toughness of a material, and can be divided into three phases:

1. Specimen preparation,
2. The test procedure; and
3. The interpretation of data.

1. Specimen Preparation

Figure 1:
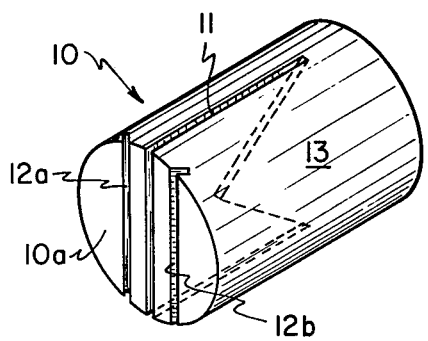

Practicing the method of the present invention involves preparation of a specimen 10 that is the same as or like the specimen shown in FIG. 1. The configuration of specimen 10, it should be understood, is preferred, but other configurations of specimens, not shown, could also be used in practicing the method of the present invention without departing from the subject matter coming within the scope of this disclosure. The particular configuration of specimen 10 is such that when it is appropriately loaded and a crack forms therein, the crack will initiate at a predetermined point, line, or the like, in a remainder portion 13 and that: as loading continues, the crack will propagate along a predetermined path through the specimen. During an initial phase of the practice of the method of the present invention, which phase may or may not include initiation of the crack, crack growth will be intrinsically stable, even in specimens formed from the most brittle material where: a crack propagating through the specimen reaches a critical location along the predetermined crack path, which location represents the specimen having been subjected to a maximum load, the load necessary to further advance the crack after that point is less than that maximum load, the critical location along the crack path through the specimen is essentially determined by the specimen geometry alone, provided that certain minimum size criterion are met; and the load necessary to effect crack advance through the specimen exerts primarily plane strain conditions in that specimen close to the crack tip. The minimum specimen size for completing a valid stress intensity test being dependent upon the ratio of $(K_{IC}/\sigma_{ys})^2$, where $K_{IC}$ is the specimen materials' critical stress intensity factor, or facture toughness for the specimen material and $\sigma_{ys}$ is the specimen yield strength. The minimum size also depends upon the specimen geometry, such that, in general, the specimen minimum size needs to be experimentally determined for each specimen geometry. Experimentally, it has been determined that the minimum specimen size for a short rod specimen like that shown herein is approximately:

$$D = 4(K_{IC}/\sigma_{ys})^2,$$

where D is the specimen diameter.

Figure 2:
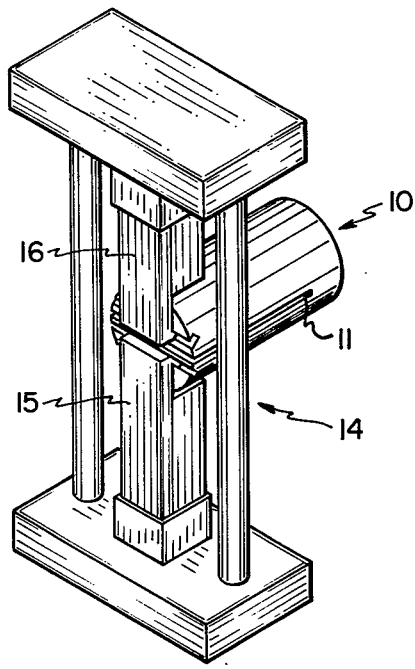

The short rod shown in FIG. 1, it should be assumed, has been processed by a diamond saw, or the like, to produce the finished specimen 10. The specimen 10 as shown therein is, either a ductile or brittle material, preferably slotted longitudinally at 11 and has grip slots 12(a) and 12(b) formed in the specimen face 10(a) above and below that longitudinal slot 11. Specimen 10 is preferably slotted so as to leave, as a remainder in said longitudinal slot 11, a "V" 13 having its pointed apex facing towards the specimen face 10(a). The plane of the "V" 13, as shown best in FIG. 3, during a test procedure, is arranged to be perpendicular to the direction of a load applied at or near the face 10(a) of the specimen, which load can be applied as by a test machine 14 that is shown in FIG. 2; by installation and inflation of a bladder, not shown, within the slot 11, that bladder expanding to push the sample apart from within the slot; or a like device. The test machine 14, shown best in FIG. 2, has a lower grip 15 and an upper grip 16 as specimen loading portions thereof that are shown in FIG. 3 enlarged and removed from test machine 14.

2. The Test Procedure

Figure 3:
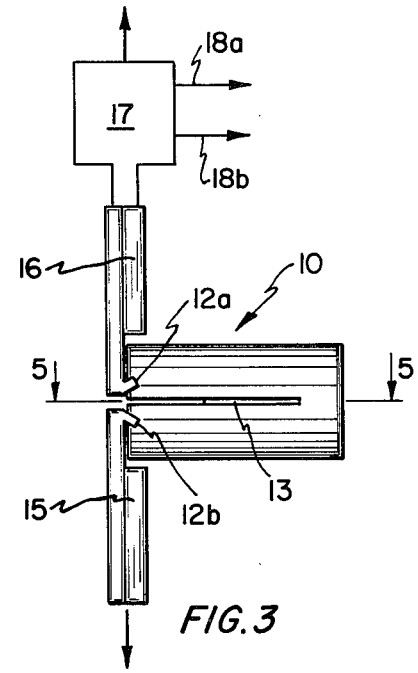

Shown best in the FIGS. 2 and 3, the specimen 10 is preferably arranged between the grips 15 and 16 of the test machine 14, with said grips arranged to be moved apart by appropriate hydraulic, electrical, or mechanical means, not shown, so as to provide a load across said sample face 10(a). Such load acts, as outlined hereinabove, on the specimen "V" 13, to fulfill a loading requirement on specimen 10 so as to initiate and propagate a crack through that specimen to the critical point. This load provides, it should be understood, primarily plane strain conditions in the specimen "V" 13, close to the crack tip. The induced load is preferably measured by a force transducer 17 that is preferably connected by wires 18(a) and 18(b) to a recorder, not shown, or the like, for measuring load changes for later determination of the peak load and for computation, as will be explained in detail later herein, of the specimen's plane strain fracture toughness.

Figure 4:
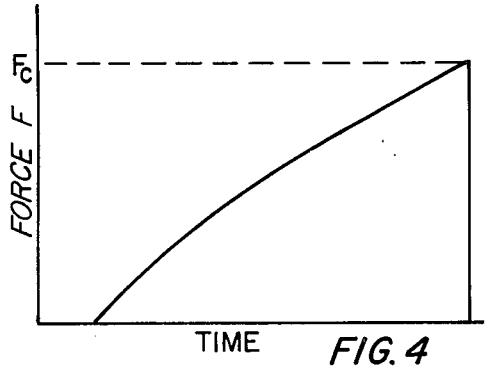

The graph of FIG. 4 shows a force F applied to specimen 10 as being a vertical component, which force F is increased incrementally against time, the graph thereby reflecting the load applied on the specimen 10 as a function of time.

Figure 5A:
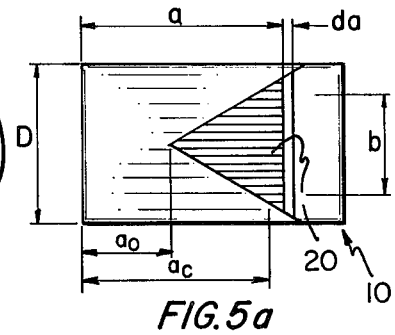

Reference is hereby made to FIG. 5(a) wherein is shown a cross section of specimen 10, where through, as shown at 20, a crack has propagated. FIG. 5(a) is intended to represent a specimen configuration used for an experiment that is conducted so as to practice the method of the present invention to determine the plane strain fracture toughness of a material from which specimen 10 is constructed. It should, however, be quite apparent, that a similar procedure could be followed equally well on another specimen configuration that also exhibits a preliminary region of crack growth stability followed by instability or fracture under controlled loading conditions.

3. The Interpretation of Data

The specimen 10 configuration, shown in FIG. 1, is preferably a short rod specimen 10, having a small length to diameter ratio in a range of from 1.4 to 1.6, which short rod specimen is slotted and loaded in such a way that a crack initiates at the point of the "V", 13, and splits the specimen longitudinally as it propagates. As illustrated in FIG. 5(a) "$a_o$" denotes the distance from the face 10a of the specimen to the point of the "V", 13; "a" is the distance from the face of the specimen 10 to the crack front; "$a_c$" is the distance from the face of the specimen 10 to a critical crack point; "b" is the crack width, and "D" is the specimen diameter.

Assuming a test procedure utilizing the method of the present invention, as described above, was conducted on a specimen, like specimen 10, and that the test involves slowly increasing a load, F, on the specimen. At some point, a crack will initiate at the point of the "V", 13, and the crack growth is initially stable. The load necessary to advance the crack is intended to increase until the crack reaches a critical length, $a_c$, and thereafter the load decreases with increasing crack length. The peak load, "$F_c$", during the experiment is used in a simple equation to calculate the critical stress intensity factor, "$K_{IC}$" or the fracture toughness of the specimen material.

The equation for $K_{IC}$ is derived from linear elastic fracture mechanics principles, and assumes that the energy per unit area of new crack surface created in plane strain is a material constant, "$G_{IC}$". Under plane strain conditions, then, the energy required to advance the crack a small distance, $da$, shown in FIG. 5(a), is $$dW_1 = G_{IC} b\, da, \qquad (1)$$

where b, as stated above, is the width of the crack front. The energy, "$dW_1$", comes from the irrecoverable work done on the specimen during the test.

Figure 5B:
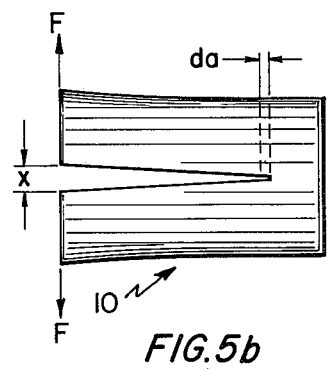
Figure 5C:
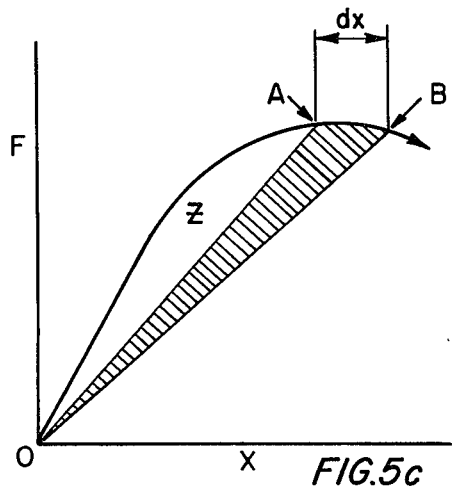

To initiate the crack, the specimen is loaded with a force, F, shown in FIG. 5(b), causing the front of the specimen to open by an amount "x" Before crack initiation, the loading path (F vs. x) proceeds up a steep linear elastic slope as depicted in the graph of FIG. 5(c). The onset of nonlinearity in the loading path signifies the initiation of the crack at the point of the "V", 13.

Assuming that the force F is continually increased until the crack length, a, and the load point opening, x, are as shown in FIGS. 5a and 5b; and the loading path is at A in 5(c). If the sample were unloaded from that point, the unloading path would be a straight line to the origin, since no plastic work and no crack growth occur on unloading. The irrecoverable work done on the specimen during the loading-unloading cycle would be the area z of FIG. 5(c), i.e., the area between the loading and unloading paths.

Suppose, however, that, instead of unloading from point A, the crack is advanced an additional increment, $da$, which would be accompanied by an additional load-point-opening increment, $dx$, FIG. 5(c), such that the loading path would advance to point B. A subsequent unloading from B would again produce a straight line to the origin, FIG. 5(c). It is clear that the additional irrecoverable work, $dW_2$, done in advancing the crack the additional distance, $da$, would be given by the shaded area of the triangle OAB, or $$dW_2 = \tfrac{1}{2} F dx.$$

From the definition of the elastic compliance of the specimen, $c = x/F$, and letting F be the average value of the load, i.e., a constant, during the crack advance, $da$, we have $dx = F dc$, or $$dW_2 = \tfrac{1}{2} F^2 dc \qquad (3)$$

According to the principles of linear elastic fracture mechanics, $dW_2$ represents a release of strain energy by the specimen which is available for creation of the new crack area. Thus, equating $dW_1$ and $dW_2$, $$G_{IC} b = (F^2/2) \cdot (dc/da) \qquad (4)$$

Here, b, F and $dc/da$ are evaluated at the crack length, a, at which the incremental crack advance took place. Equation 4 is not new; essentially the same equation was published by Irwin, G. W. and Kies, J. E., Weld. J., 33, 193(1954), and is re-derived here simply to show its applicability to specimen 10 configuration.

In order to reform Equation 4 in terms of the critical stress intensity factor, $K_{IC}$, the plane strain equation relating $G_{IC}$ and $K_{IC}$ is used:

$$G_{IC} = K_{IC}^2 (1 - \nu^2)/E. \qquad (5)$$

Thus, equation 4 becomes, after some manipulation, $$K_{IC} = \frac{F_c f(a/D)}{D^{3/2}(1-\nu^2)^{1/2}} \quad (6)$$

where $D$ is the specimen diameter, $E$ is the elastic modulus of the specimen material $\nu$ is Poisson's ratio, and where $$f(a/D) = \left[\frac{D \, d \, (cED)}{2b \, d \, (a/D)}\right]^{\frac{1}{2}} \quad (7)$$

The quantity in brackets is a function only of the ratio $a/D$, independent of the specimen material, as long as the scaled specimen configuration remains constant Therefore, as with other fracture toughness specimen geometries, this geometry can be carefully compliance calibrated, and $f(a/D)$ can be approximated by a polynomial in $a/D$. Once the coefficients in $f(a/D)$ are evaluated, a $K_{IC}$ measurement can be made by advancing a crack to some measured value of $a$, so that $f(a/D)$ can be evaluated and then measuring F necessary to further advance the crack.

The development of equation 6 has closely paralleled the development of equations for $K_{IC}$ using standard ASTM specimens. At this point, however, a significant simplification can be made in the case of the short rod test, for it has been shown that the scaled crack position, $a_c/D$, at which the peak load is encountered is again independent of the specimen material, being a function only of the specimen geometry. Thus, the value of $f(a/D)$ in equation 7 at the time of the maximum load, $F_c$, is a constant, $A = f(a_c/D)$. Therefore, we have $$K_{IC} = AF_c/D^{3/2}(1-\nu^2)^{1/2} \quad (8)$$

or $$K_{IC} = AF_c/D^{3/2} \quad (9)$$

if we follow custom in replacing $(1-\nu^2)^{1/2}$ by unity.

Equations 8 and 9 are simplified compared to the ASTM formula for $K_{IC}$ by the replacement of a fourth-order polynomial by the dimensionless constant, A. In addition, no measurement of crack length is required, and rather than determining F from the intersection of a 5 percent slope offset line with the load-displacement curve, F is simply the maximum load during the experiment, $F_c$. Therefore, fatigue pre-cracking of the short rod specimen is generally not necessary because the crack is initially stable.

Although a preferred procedure for practicing the method of my invention has been shown herein, it should be understood than the present disclosure is made by way of example and that variations are possible without departing from the subject matter coming from the scope of the following claims which matter I regard as my invention.

I claim:

1. A method for measuring the fracture toughness of a material comprising the steps of, forming a slotted specimen leaving an internal "v" shape as a remainder therein;

applying an incrementally increasing load to cause a crack to initiate and propagate in plane strain conditions along a predetermined path through said specimen;

measuring the maximum load in propagating the crack through the specimen; and calculating said material's fracture toughness from the measured maximum load, and from considerations involving the specimen size and geometry.

2. A method as defined in claim 1 further including the steps of, initiating and arresting the initial crack prior to its reaching a critical point where a load vs crack position curve goes through a maximum; and slowly increasing the loading to cause said crack to advance through said critical point.

3. A method as defined in claim 1, wherein in calculating said specimen material's fracture toughness, which is also the specimen's critical stress intensity factor, "$K_{IC}$", is equal to a dimensionless constant "A" for the specimen's geometric configuration times the peak load force "$F_c$" divided by a characteristic dimension of the specimen which identifies its physical size "D" to the 3/2 power, $$K_{IC} = AF_c/D^{3/2}.$$

4. A method as defined in claim 3 including Poisson's ratio in the calculation of the specimen material's fracture toughness, "$K_{IC}$" is equal to a dimensionless constant "A" for the specimen's geometric configuration times the peak load force "$F_c$" divided by a characteristic dimension of the specimen which identifies its physical size "D" to the 3/2 power times the square root of 1 minus Poisson's ratio "$\nu$" squared, $$K_{IC} = AF_c/D^{3/2}(1-\nu^2)^{1/2}.$$

* * * * *